United States Patent
Di Girolamo et al.

(10) Patent No.: US 10,774,020 B2
(45) Date of Patent: Sep. 15, 2020

(54) PROCESS FOR OBTAINING HIGH-PURITY 1-BUTENE FROM C4 HYDROCARBON MIXTURES

(75) Inventors: Marco Di Girolamo, San Donato Milanese (IT); Maura Brianti, Busto Arsizio (IT); Massimo Conte, Peschiera Borromro (IT)

(73) Assignee: SAIPEM S.p.A., San Donato Milanese (Milan) (IT)

( * ) Notice: Subject to any disclaimer, the term of this patent is extended or adjusted under 35 U.S.C. 154(b) by 9 days.

(21) Appl. No.: 13/144,101

(22) PCT Filed: Jan. 11, 2010

(86) PCT No.: PCT/EP2010/000187
§ 371 (c)(1),
(2), (4) Date: Sep. 26, 2011

(87) PCT Pub. No.: WO2010/081705
PCT Pub. Date: Jul. 22, 2010

(65) Prior Publication Data
US 2012/0010451 A1 Jan. 12, 2012

(30) Foreign Application Priority Data
Jan. 13, 2009 (IT) .................. MI2009A027

(51) Int. Cl.
*C07C 7/177* (2006.01)
*C07C 11/08* (2006.01)
(Continued)

(52) U.S. Cl.
CPC .............. *C07C 7/177* (2013.01); *C07C 7/005* (2013.01); *C07C 7/04* (2013.01); *C07C 7/14891* (2013.01); *C07C 7/163* (2013.01); *C07C 41/06* (2013.01)

(58) Field of Classification Search
CPC ... C07C 5/2506; C07C 5/2512; C07C 5/2518; C07C 7/04; C07C 41/42
(Continued)

(56) References Cited

U.S. PATENT DOCUMENTS

| 4,558,168 | A | * | 12/1985 | Gussow et al. | ............... 585/324 |
| 2007/0149839 | A1 | * | 6/2007 | Rix et al. | ....................... 585/664 |
| 2008/0021255 | A1 | | 1/2008 | Santiago-Fernandez et al. | |

FOREIGN PATENT DOCUMENTS

WO  97 32838  9/1997
WO  WO 97/32838 * 9/1997

OTHER PUBLICATIONS

International Search Report dated Apr. 29, 2010 in PCT/EP10/000187 filed Jan. 11, 2010.

* cited by examiner

*Primary Examiner* — Youngsul Jeong
(74) *Attorney, Agent, or Firm* — Oblon, McClelland, Maier & Neustadt, L.L.P.

(57) ABSTRACT

A process is described for obtaining high-purity 1-butene starting from $C_4$ hydrocarbon mixtures containing isobutene, n-butane, isobutane, 1,3-butadiene, 1-butene, 2-butenes and also optionally $C_3$ and $C_5$ hydrocarbons, comprising the following stages: conversion of isobutene effected in a double stage, wherein each stage consists of one or more reactors followed by a distillation column for the recovery of the reaction product; recovery of the excess alcohol; recovery of 1-butene using at least two distillation columns; characterised in that it also uses a further conversion stage, consisting of one or more reactors in series, for completing the isobutene removal.

28 Claims, 14 Drawing Sheets

Figure 1:
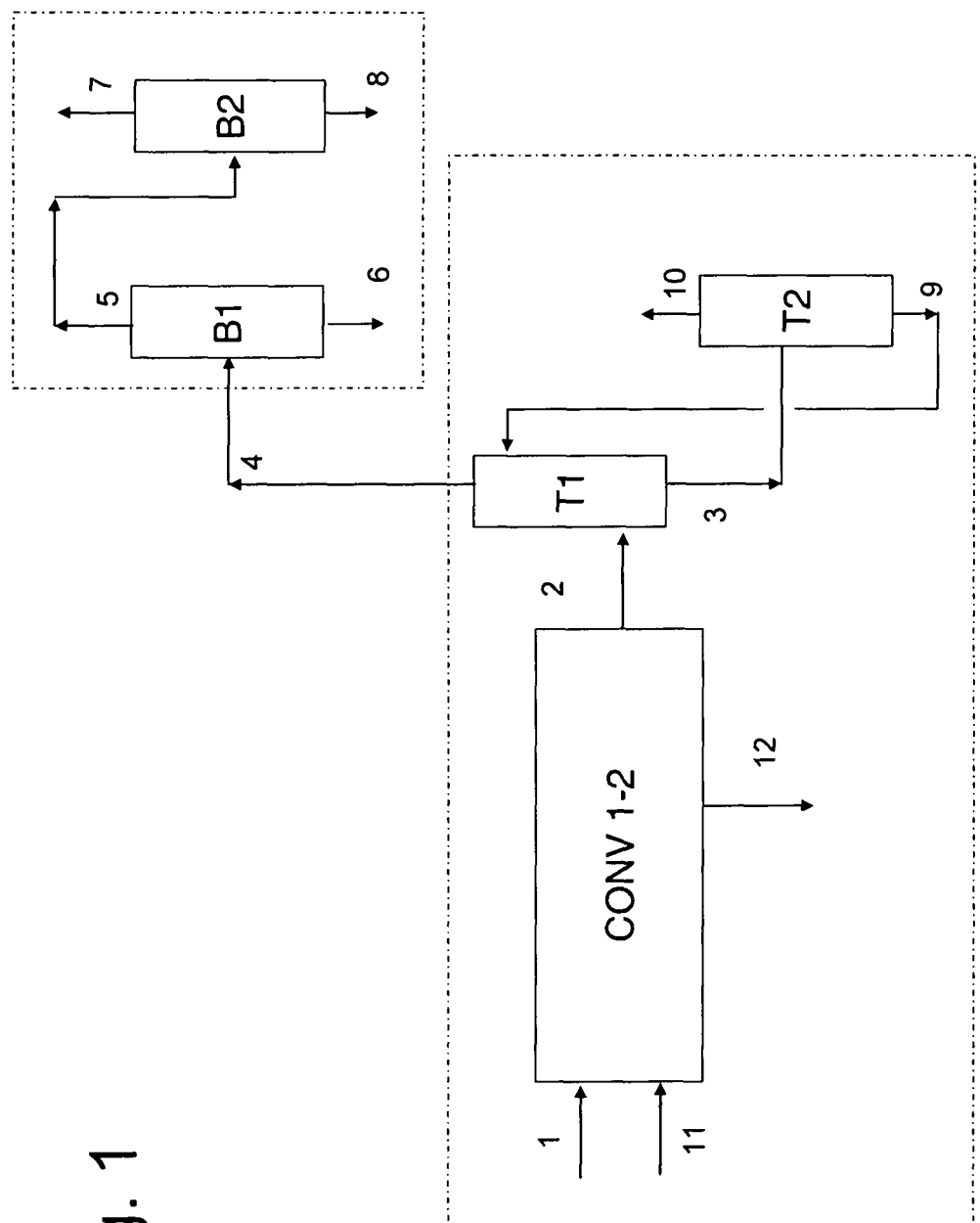

(51) Int. Cl.
*C07C 11/00* (2006.01)
*C07C 5/25* (2006.01)
*C07C 7/00* (2006.01)
*C07C 7/04* (2006.01)
*C07C 7/148* (2006.01)
*C07C 7/163* (2006.01)
*C07C 41/06* (2006.01)

(58) Field of Classification Search
USPC .................................................. 585/324, 664
See application file for complete search history.

PROCESS FOR OBTAINING HIGH-PURITY 1-BUTENE FROM C4 HYDROCARBON MIXTURES

The present invention relates to a process for obtaining high-purity 1-butene from $C_4$ hydrocarbon mixtures containing isobutene, n-butane, iso-butane, 1,3-butadiene, 1-butene, 2-butenes and also optionally $C_3$ and $C_5$ hydrocarbons, capable of maximizing the recovery of polymer grade 1-butene.

1-butene is an important petrochemical intermediate mainly used as co-monomer in polymerization reactions, in particular in the synthesis of linear low density polyethylene (LLDPE), with a market in continuous and constant expansion within a consolidated scenario; this has led to the necessity of finding new and/or more efficient systems for its recovery and production in order to be able to face the constant market requirements.

Although a wide variety of technologies are available for obtaining this olefin, the most common technology relates to separation from $C_4$ hydrocarbon streams containing linear olefins. FCC or Steam Cracking form the main sources of these streams as shown in Table 1.

From examining the Table, it can be observed that the Steam Cracking fraction has a much higher 1-butene content and consequently is the one mainly used for the recovery of this olefin.

TABLE 1

|  | Steam Cracking | Steam Cracking after removal of 1,3-Butadiene | FCC |
| --- | --- | --- | --- |
| Isobutene, % wt | 20-30 | 20-50 | 10-25 |
| 1-Butene, % wt | 13-20 | 20-50 | 10-15 |
| 1,3-Butadiene, % wt | 25-50 | 0.5-0.001 | <0.5 |
| Isobutane, % wt | 0.5-2 | 0.5-3 | 25-35 |
| 2-Butenes, % wt | 10-15 | 15-40 | 20-35 |
| n-Butane, % wt | 2-5 | 2-8 | 5-15 |

Depending on the efficiency of the recovery steps of the $C_4$ fraction, $C_3$ and $C_5$ hydrocarbons can also be present in all these feedstocks, in a variable quantity (0.5-10% by weight).

Inside the $C_4$ fraction it is not economically advantageous, however, to separate 1-butene from butadiene and isobutene by means of simple distillation, due to the closeness of boiling point, as indicated in Table 2.

TABLE 2

|  | Relative Volatility | B.P., ° C. |
| --- | --- | --- |
| Isobutane | 1.20 | −11.7 |
| Isobutene | 1.07 | −6.9 |
| 1-Butene | 1.04 | −6.3 |
| 1,3-Butadiene | 1.00 | −4.4 |
| n-butane | 0.87 | −0.5 |
| trans 2-butene | 0.85 | 0.9 |
| cis 2-butene | 0.79 | 3.7 |

Industrially, resort is therefore made to the use of removal processes of butadiene and isobutene from $C_4$ streams to be able to obtain a 1-butene having the minimum purity required, for use in polymerization as indicated in Table 3.

TABLE 3

|  | % weight |
| --- | --- |
| 1-Butene | >99.5 |
| Isobutene | 0.3 |
| Butadiene | 0.005 |
| Other $C_4$ | 0.2 |

In the case of feedstocks from Steam Cracking, the removal of butadiene is normally carried out by means of extraction with nitrogenated compounds or through selective hydrogenation to linear butenes.

For the removal of isobutene, on the other hand, etherification reaction with methanol is used, with the formation of methyl tert-butyl ether (MTBE); this reaction is in fact characterized by great simplicity and an extremely favourable thermodynamic equilibrium which is such as to allow, with a double-step reaction configuration, high conversions of isobutene to be reached, which are necessary for falling within the specifications of polymer grade 1-butene.

Figure 2:
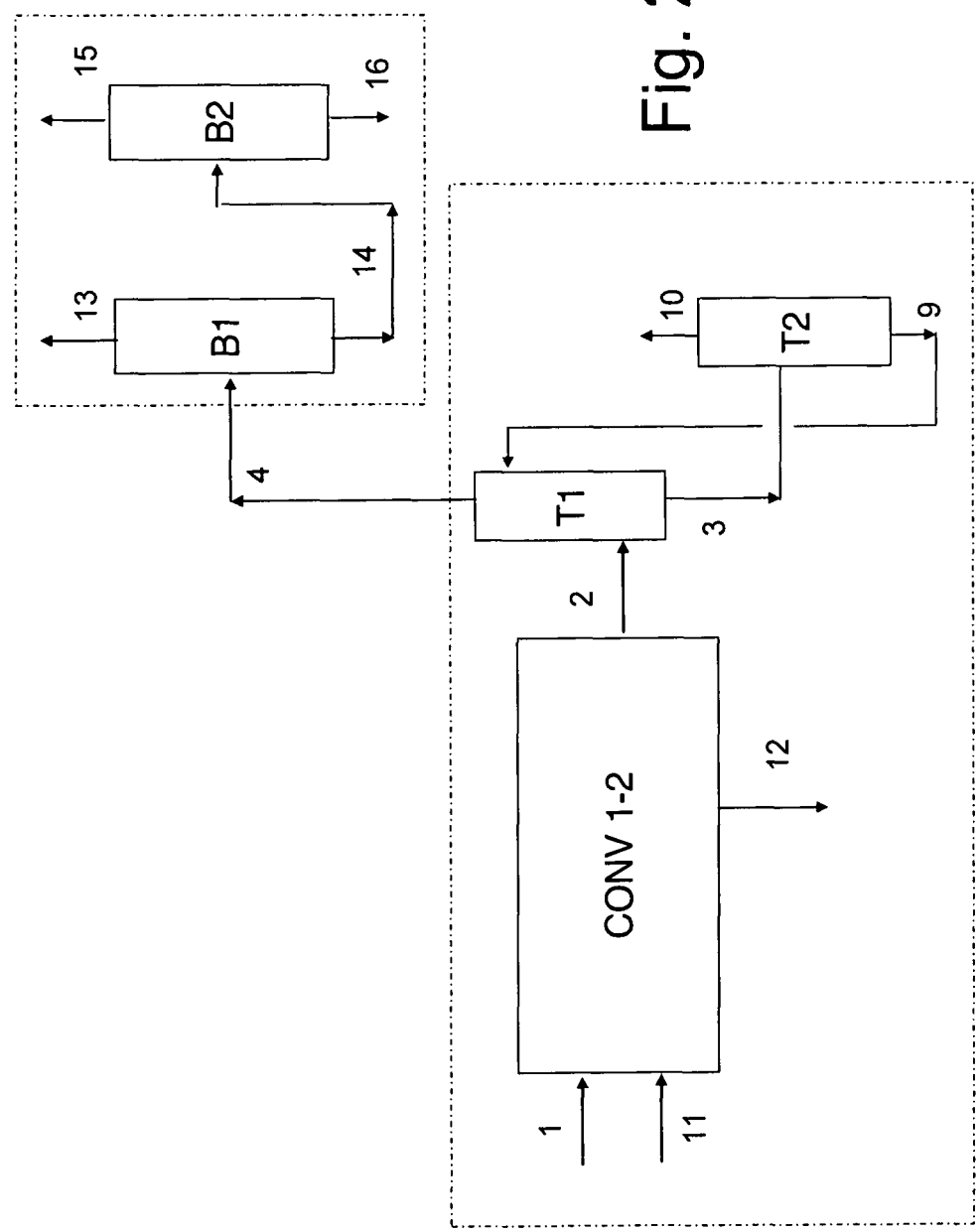

Both FIG. 1 and FIG. 2 indicate a classical scheme for the production of MTBE and the recovery of 1-butene starting from a $C_4$ hydrocarbon feedstock from Steam Cracking in which the butadiene has been previously and quantitatively removed.

In this scheme, the $C_4$ cut (1) is fed together with fresh methanol (stream 11) to the traditional etherification section of isobutene (CONV 1-2), consisting of two reaction steps, each comprising one or more reactors with intermediate cooling followed by a fractionation column for the recovery of the ether produced; the mixture obtained by joining the bottoms of the fractionation columns of the two steps forms the end-product of the plant (MTBE) (12).

The effluent of the traditional conversion step (2), mainly consisting of $C_4$ residues and azeotropic alcohol, is sent to the recovery section of the alcohol consisting of two columns (T1) and (T2); in this section, the methanol is first separated from the $C_4$ products and recovered as hydroalcohol mixture (3) from the bottom of the washing column T1, then recovered and optionally recycled to the etherification section, as distillate (10) of the column T2 whose bottom, on the other hand, consists of water (9) which is recycled to the washing column.

The overhead product of the column T1 (4), consisting of $C_4$ hydrocarbons and called Raffinate 2, forms, on the other hand, the charge of the recovery section of 1-butene in which, through the two fractionation columns B1 and B2, the olefin is separated from the light compounds ($C_3$, isobutane) and from the heavy compounds (n-butane, 2-butenes and $C_5$).

Depending on the relative concentrations of the light and heavy compounds, two different separation schemes can be assumed.

In the scheme of FIG. 1, the feed, deriving from a Steam Cracking unit, is characterized by high quantities of linear olefins and it is consequently more convenient to first separate the heavy compounds (6) as bottom product of column B1 and send the overhead product (5) to column B2 and then recover the 1-butene as bottom product (8) of the column, separating the light products (7) at the top.

In the case of FCC or mixed streams, characterized by greater quantities of isobutane, it is more convenient, as shown in FIG. 2, to separate the 1-butene together with the heavy compounds (14) as bottom product of the first column B1 from the light compounds (13) and subsequently recover the pure linear olefin as distillate of the column B2 (15), separating the heavy compounds (16) at the bottom.

For both schemes, the presence in the $C_4$ cut of possible oxygenated compounds (water, methanol, dimethylether, MTBE and tert-butyl alcohol), at a level of hundreds of ppm, deriving from the etherification section, does not represent a problem for the purity of the 1-butene as these compounds are eliminated either together with the light products (water, methanol, dimethylether) or with the heavy products (MTBE and tert-butyl alcohol). Due to the proximity of the boiling points, a complete recovery of 1-butene from the $C_4$ fraction is obviously too onerous; recoveries of 70-90%, on the other hand, are typical of this technology and represent a fair compromise between production and investment.

With respect to this consolidated scenario, against a constant increase in the request for 1-butene, there has been a drastic reduction in the market of MTBE due to the partial ban of this ether in the United States and to the introduction in European gasolines of oxygenated compounds from renewable sources (biofuel) such as ethanol and ethyl tert-butyl ether (ETBE) instead of the same MTBE.

This has led to the necessity of reconverting the existing MTBE plants, integrated with the recovery of 1-butene, into alternative productions capable of guaranteeing the same conversion level of isobutene.

There are numerous possible technological solutions, those which are the most advantageous from an economical point of view, however, are essentially etherification, effected with ethanol instead of methanol and consequently the production of ETBE, and the synthesis of high-octane hydrocarbon products by the dimerization of isobutene.

Really, it is also possible to contemporaneously use these two solutions and simultaneously produce both compounds (ETBE and dimers) in a single plant.

Both of these processes have the great advantage of being able to use, except for small modifications, existing MTBE plants, but have the considerable limit of not allowing the same conversion level as the MTBE case (then the specification of 1-butene) to be obtained, as:

in the case of ETBE, under the same operating conditions used (alcohol/olefin molar ratio, temperature), the thermodynamic equilibrium (therefore the maximum conversion obtainable) is less favoured;

in the case of dimerization, in order to convert the last quantities of isobutene, an excessive quantity of 1-butene is lost in the codimerization and bond isomerization reactions.

This latter reaction is particularly important since the thermodynamic equilibrium of the linear olefins is shifted, under the conditions used in the dimerization of isobutene, towards the formation of internal olefins (2-butenes).

It is therefore evident that there is great interest in obtaining innovative and more efficient reaction schemes which allow both 1-butene to be obtained according to specification for polymerization reactions and also to increase the productivity of the recovery units of the olefin and there is evidently no obvious solution for this problem.

We have now succeeded in obtaining a high-purity 1-butene thanks to the introduction of an additional conversion section of isobutene suitably integrated with the existing conversion and fractionation sections.

The process, object of the present invention, for obtaining high-purity 1-butene starting from $C_4$ hydrocarbon mixtures containing isobutene, n-butane, iso-butane, 1,3-butadiene, 1-butene, 2-butenes and also optionally $C_3$ and $C_5$ hydrocarbons, comprises the following stages:

conversion of isobutene effected in a double stage, by etherification with alcohol and/or dimerization in the presence of alcohol and/or water and/or alkyl ether, wherein each stage consists of one or more reactors followed by a distillation column for the recovery of the reaction product;

recovery of the excess alcohol if this is used in the conversion carried out by means of etherification and/or by dimerization;

recovery of 1-butene using at least two distillation columns;

and characterised by the use of a further conversion stage, consisting of one or more reactors in series, for completing the isobutene removal.

In the further conversion stage, necessary for reaching the commercial specifications, can be used either the etherification reaction in the presence of a linear alcohol having from 1 to 5 carbon atoms, preferably ethanol and/or methanol, or optionally also the addition reaction of water to the isobutene with the formation of tert-butyl-alcohol (TBA).

This additional conversion stage can be positioned immediately before the recovery section of 1-butene or immediately before the recovery section of the alcohol.

After the additional conversion stage, there can be a distillation column for removing the compounds produced in said further stage, whose presence is advisable when these compounds are a poison for the subsequent applications of the residual $C_4$ stream.

The insertion of this new column depends on the final use of the stream containing heavy $C_4$ compounds (2-butenes and n-butane) in which all the oxygenated products formed in the additional conversion step would accumulate; oxygenated products, in fact, are poisons in some of the traditional treatment processes of these streams (polymerization, alkylation and metathesis) and they should therefore be removed.

The distillation column for removing the compounds produced in the further conversion stage can be fed with the $C_4$ hydrocarbon stream, containing 2-butenes and n-butane, leaving the 1-butene recovery section.

The conversion of isobutene in two stages can be effected by means of etherification with a linear alcohol, preferably having from 1 to 5 carbon atoms, or by selective dimerization in the presence of a linear alcohol, preferably having from 1 to 5 carbon atoms, and/or branched alcohol, preferably having from 3 to 6 carbon atoms, and/or in the presence of water and/or in the presence of alky ethers, preferably having from 5 to 10 carbon atoms.

The recovery of the alcohol in excess can be effected through a classical 2-column scheme in which the first is a washing column with water or alternatively by means of an absorption system, for example with molecular sieves.

If the two-stage conversion is carried out by dimerization in the presence of water alone, said recovery stage of the alcohol is not present.

In order to effect the conversion reactions described above, a wide variety of operating conditions can be used, which will be described hereunder.

With respect to the etherification and dimerization reactions, the pressure is preferably superatmospheric to keep the reagents in liquid phase, generally below 5 MPa. The reaction temperature preferably ranges from 30 to 120° C.

The feeding space velocities of the hydrocarbon streams are preferably lower than 60 $h^{-1}$, more preferably ranging from 1 to 40 $h^{-1}$. Preferred catalysts are macroreticular sulfonated resins, such as for example Amberlyst 15 and Amberlyst 35 produced by Rohm & Haas. The reactors used for the etherification and/or dimerization can be "once through" or with recycling and of the tubular, adiabatic, "Boiling Point", expanded bed type, or contained inside distillation columns.

It is also possible to optionally introduce:

an additional selective hydrogenation section of butadiene, in the case of a concentration higher than the specifications, consisting of one or more reactors in series and positioned immediately before the recovery section of the linear olefin;

an additional bond isomerization section of the stream containing 2-butenes and n-butane, leaving the 1-butene recovery stage, to increase the yield to external olefin;

an additional skeletal isomerization section of the stream containing 2-butenes and n-butane, leaving the 1-butene recovery stage, to increase the yield to 1-butene and isobutene.

The combined introduction of the additional hydrogenation stage of the dienes and further conversion stage of the isobutene also allows the production of 1-Butene of the plant to be increased by exploiting the bond isomerization reaction from 2-butenes to 1-butene; the presence of these two new conversion units, in fact, allows overcoming the limit for the applicability of the isomerization technology i.e. the formation of small quantities (100-5000 ppm) of isobutene and butadiene, sufficient however for sending the 1-butene out of specification.

The first distillation column of the 1-butene recovery stage can also act as stabilizer of the additional hydrogenation section.

The two columns of the 1-butene recovery stage can be thermally integrated.

The total or partial condensation of the stream leaving the top of one column of the 1-butene recovery stage can supply the heat necessary for reboiling the other column.

The total or partial condensation of the stream leaving the top of one column of the 1-butene recovery stage can supply the heat necessary for reboiling both the other column and the column for removing the heavy products formed in the additional conversion stage.

The columns of the 1-butene recovery section can also be thermally integrated with the alcohol recovery column T2.

The total or partial condensation of the vapours leaving the top of the alcohol recovery column T2 can be used for reboiling one of the two 1-butene recovery columns.

The columns of the 1-butene recovery section can be thermally integrated each other and also with the alcohol recovery column T2.

The heat necessary for reboiling the two columns of the 1-butene recovery section can be supplied by the total or partial condensation of the vapours leaving the tops of the alcohol recovery column and one of the two columns of the 1-butene recovery section.

The selective hydrogenation reaction of the dienes is generally carried out in one or more reactors in series with intermediate cooling and in the case of high concentrations of dienes by recycling inert or relatively unreactive compounds.

The hydrogenation is normally carried out with the $C_4$ stream maintained in liquid phase at temperatures ranging from 50 to 150° C. and feeding space velocities preferably lower than 40 $h^{-1}$.

The catalysts which can be used for the selective hydrogenations are based on noble metals, such as for example, platinum and palladium, but catalysts based on nickel or copper can also be optionally used.

As far as the bond isomerization reactions are concerned, catalysts consisting of oxides of silicon, aluminum and other metals (EP-4814542) can be used, whereas for the skeletal isomerization, catalysts consisting of aluminum and boron oxides can be adopted (U.S. Pat. No. 5,600,054).

For both of the isomerization reactions, the feeding space velocities of the hydrocarbon streams are preferably lower than 40 $h^{-1}$, more preferably ranging from 1 to 20 $h^{-1}$, the reaction temperatures ranging from 400 to 600° C., whereas the reactors used are normally of the fixed or expanded bed adiabatic type.

For a clearer illustration of the present invention, a series of embodiments of plant schemes are provided, with the help of FIGS. 3-14, which should not be considered as limiting the invention itself.

In the case of $C_4$ streams which do not respect the specification requirements of residual isobutene (as in the case of a revamping from MTBE to ETBE) an additional conversion section (CONV 3) must be inserted between the two existing sections.

Figure 3:
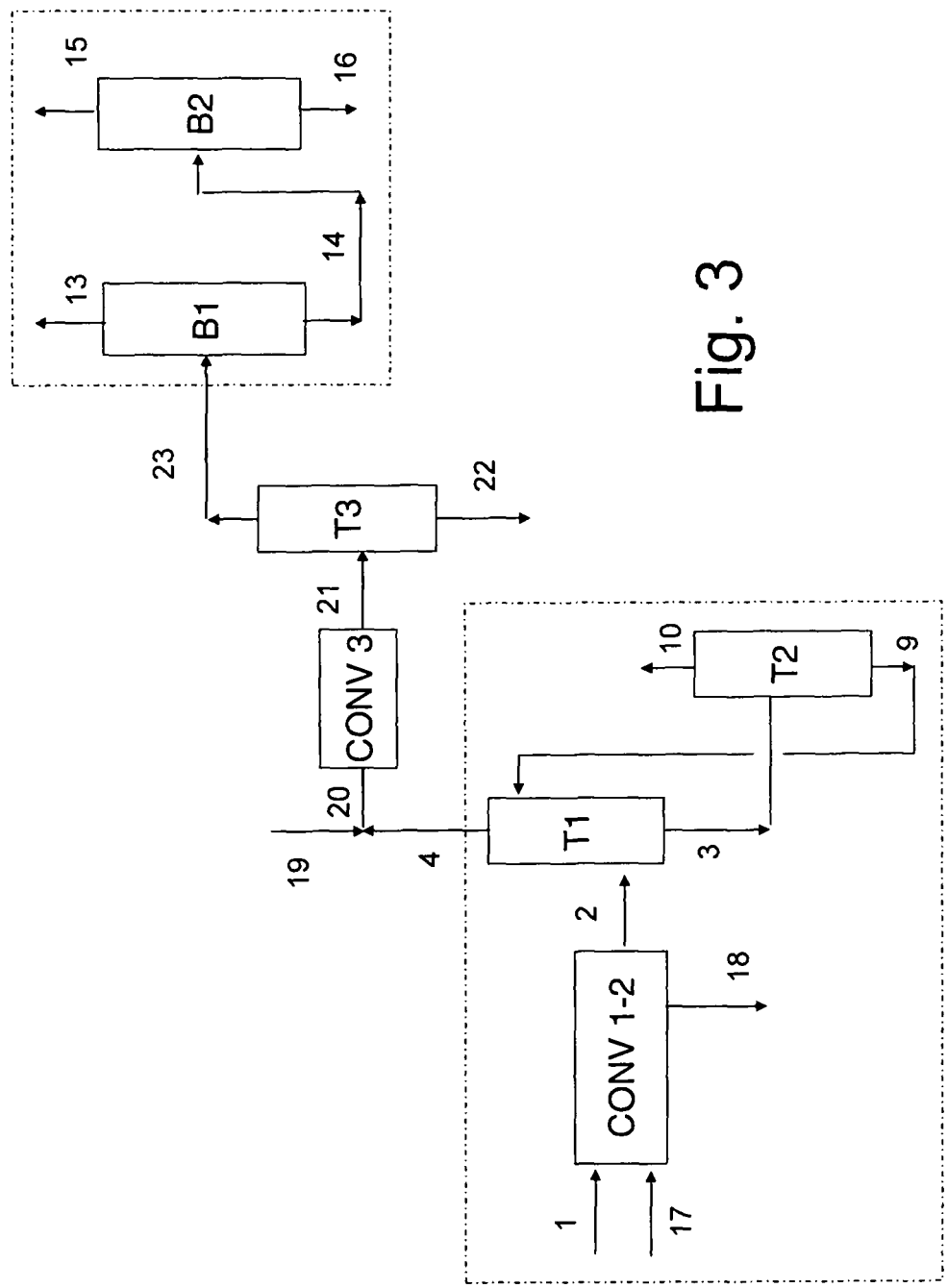
Figure 4:
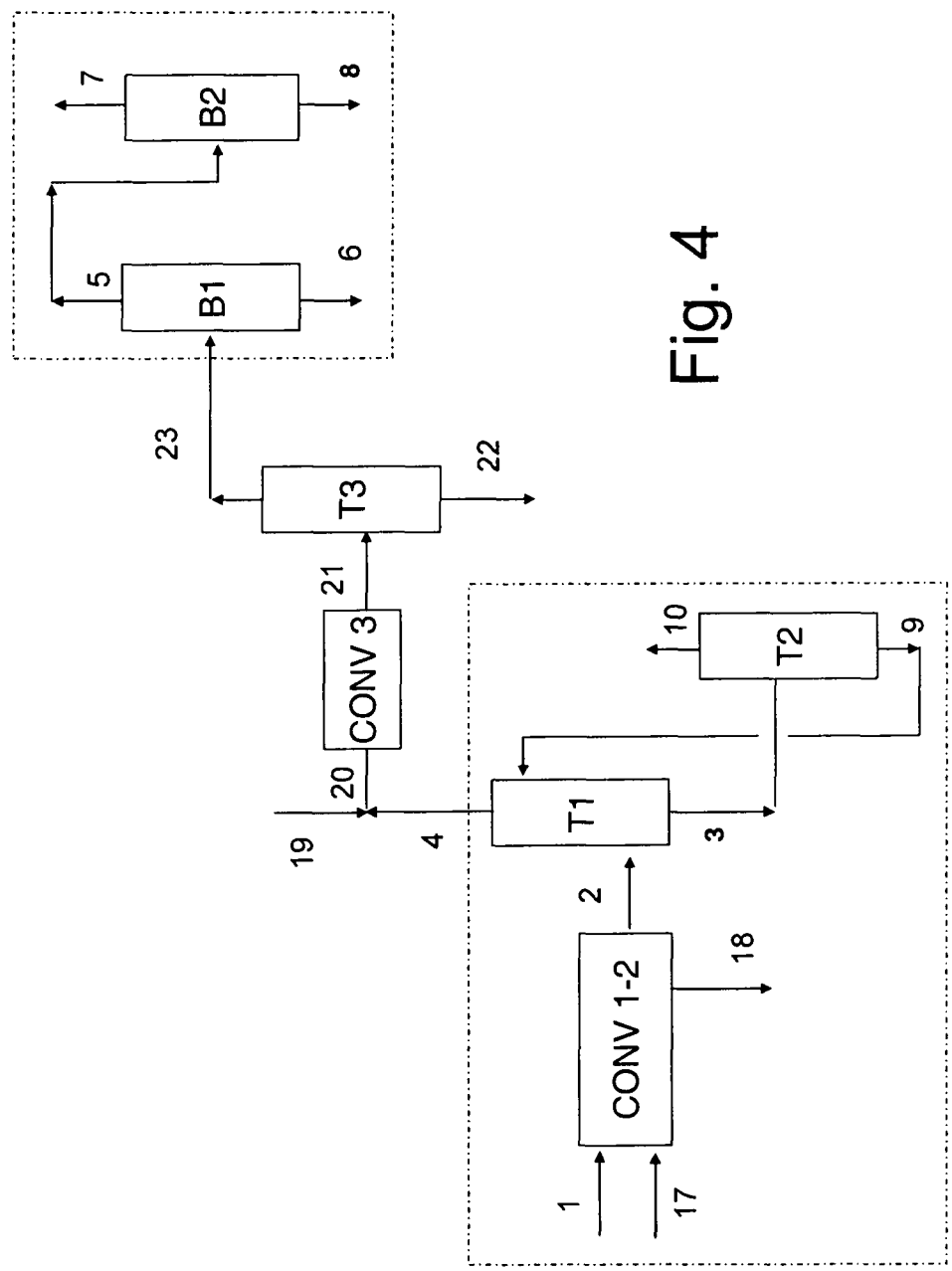

In the simplest configuration shown in FIGS. 3 and 4, the two-stage conversion section (CONV 1-2), with respect to the traditional scheme of FIGS. 1 and 2, remains unaltered with the only modifications of fresh ethanol fed (17) instead of methanol and ETBE (stream 18) obtained as product instead of MTBE; moreover fresh alcohol (19) is added to the residual $C_4$ hydrocarbons (4) which are sent (20) to the additional conversion section (CONV 3), consisting of one or more reactors, in which the residual isobutene is converted until the specification for 1-butene is reached.

The stream (21) leaving the additional section is then sent to a new fractionation column T3, for the separation of the product of CONV 3 (stream 22) which can be joined with the stream (18). The distillate of T3 (23) is the feed to the separation section of 1-butene which can be recovered at the top (15) (FIG. 3) or at the bottom (8) (FIG. 4) of the column B2.

Obviously if there is no specification on the content of oxygenated products in the stream consisting of heavy $C_4$ products leaving the unit, stream (16) of FIG. 3 and stream (6) of FIG. 4, the column T3 is not necessary.

The additional conversion section can be integrated much more effectively with the existing etherification section with a surprising improvement in both the operating flexibility and quality of the products.

Figure 5:
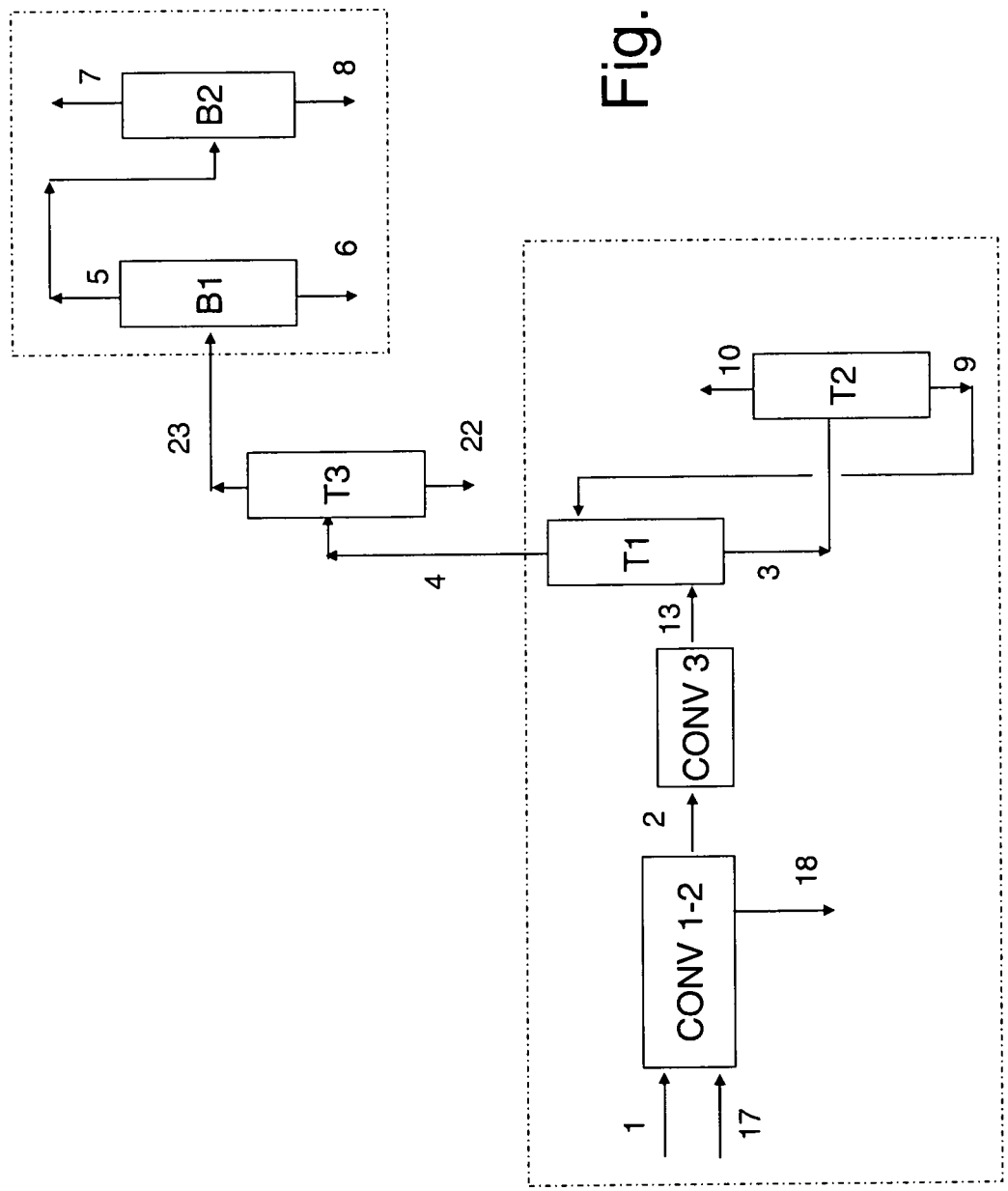
Figure 6:
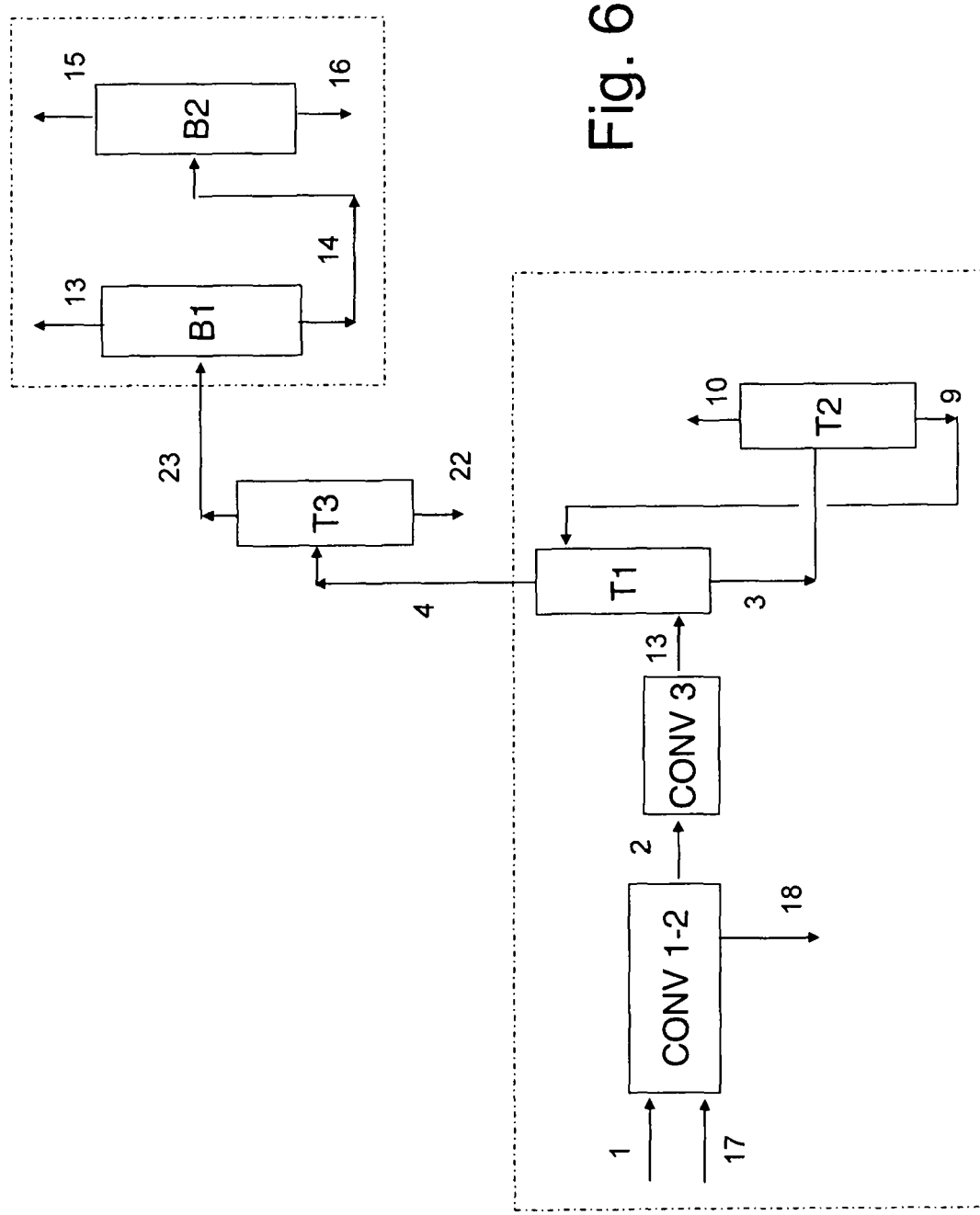

An example of this integration is provided in FIGS. 5 and 6 in which the additional conversion section CONV 3 is positioned before the washing column T1 so as to directly treat the $C_4$-ethanol mixture (2) leaving the traditional conversion section CONV 1-2.

With this configuration, the alcohol is already present in the stream to be etherified (its addition is no longer strictly necessary) and it is possible to recover the excess alcohol in the washing column T1 thus avoiding losses with the light products, stream (13) of FIG. 3 or stream (7) of FIG. 4, which, on the other hand, occurred with the previous configurations.

Once the alcohol has been removed, the $C_4$ products (stream 4), with the correct content of isobutene for a polymer grade 1-butene, are first fed to the column T3, to eliminate the product of CONV 3 (22), then sent to the fractionation section where the 1-butene can be recovered both at the bottom (8) of FIG. 5 and alternatively at the top (15) of FIG. 6 of the column B2.

Figure 7:
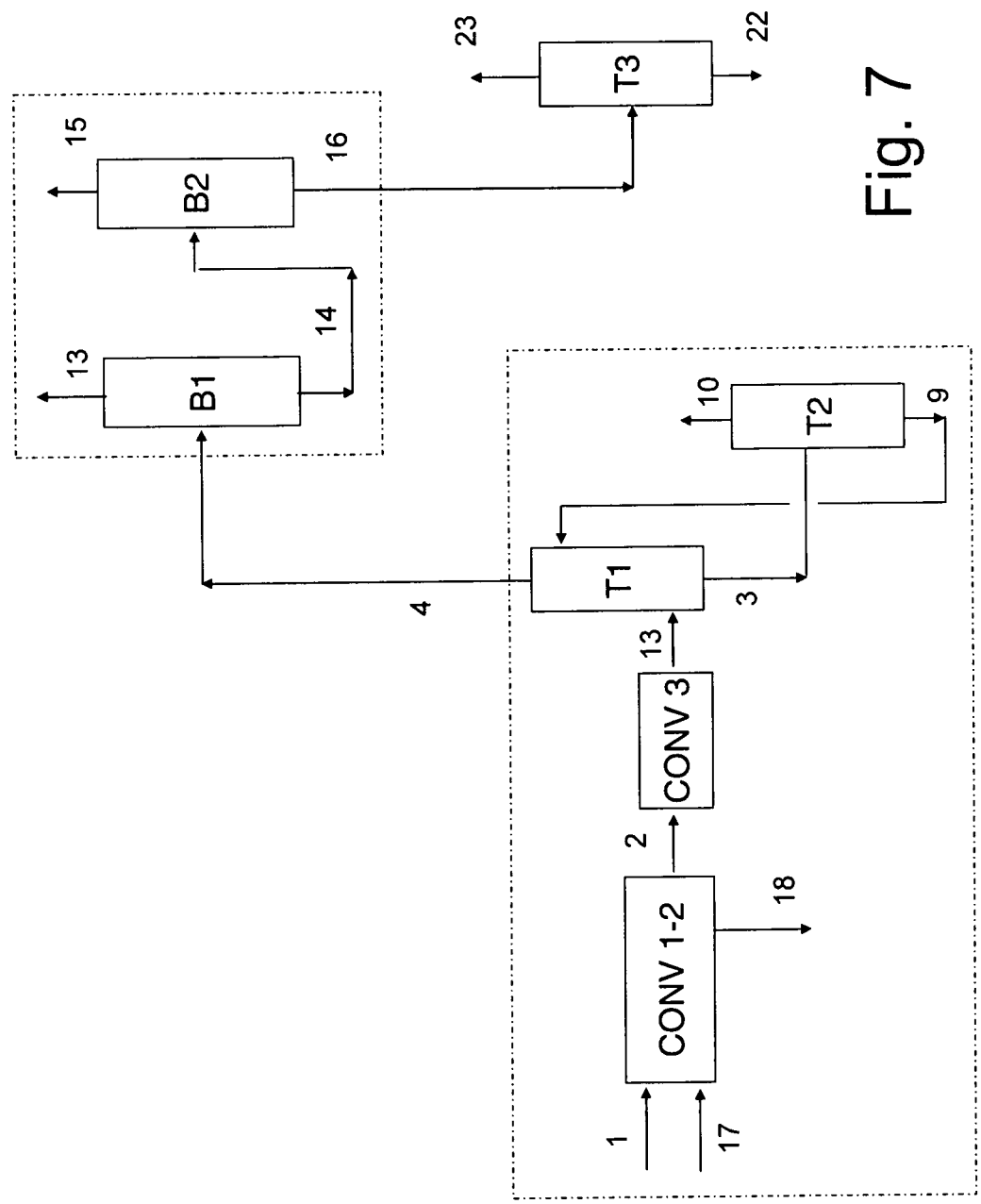
Figure 8:
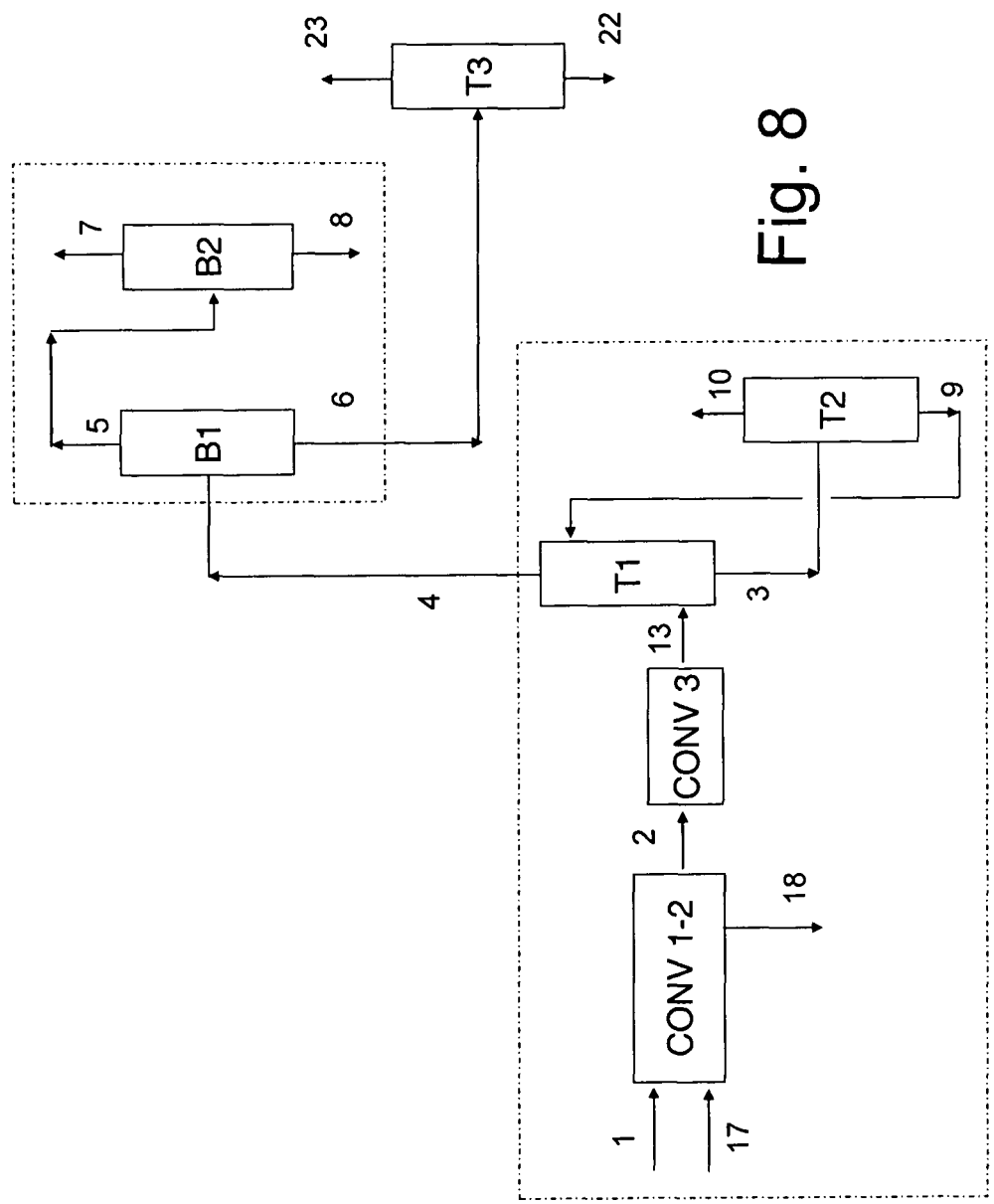

The integration, however, can become even more advantageous if the column T3 is positioned after the 1-butene recovery section as shown in FIGS. 7 and 8.

In this case, in fact, the $C_4$ products (4) leaving the washing column T1 are sent directly to the 1-butene recovery section which can be obtained as distillate (15) of FIG. 7 or at the bottom (8) of FIG. 8 of the column B2. The stream of C$_4$ heavy products (16) of FIG. 7 or (6) of FIG. 8, mainly containing 2-butenes and n-butane, is instead sent to column T3 for the recovery of the ethers produced (22) in CONV 3.

With this configuration therefore, the column T3 is fed with only the heavy fraction, which is about 50% of the whole charge (4) leaving the washing section, with evident advantages both in terms of investment and consumption.

The columns B1 and B2 of the separation section can also be independent (with separate reboilers and condensers) or thermally integrated with the heat necessary for reboiling a column which is supplied by the condensation of part of the overstream leaving the other.

This particular technological solution can also be optionally used for further improving the integration between the 1-butene recovery section and the removal column of the products of CONV 3. In the case of the configuration of FIG. 7, for example, it is possible to use the gaseous stream coming from the top of the column B2 for reboiling not only the column B1 but also T3 with an evident saving in consumption. This type of solution can obviously also be applied to the other examples indicated in the invention.

A further example of thermal integration can be obtained between the 1-butene recovery section and the alcohol recovery column T2. In this case, in fact, the heat necessary for reboiling the two columns of the 1-butene recovery section can be supplied by the total or partial condensation of the vapours leaving the top of the alcohol recovery column and one of the two columns of the 1-butene recovery section.

Should the C$_4$ streams not respect also the specification requirements relating to 1,3-butadiene, on the other hand, a selective hydrogenation section must be introduced before the 1-butene recovery section.

The hydrogenation, in its traditional configuration, consists of one or more reactors positioned in series with intermediate cooling, followed by a column, called stabilizer, whose function is to remove the excess hydrogen from the C$_4$.

Also in this case, the integration between the selective hydrogenation and the 1-butene recovery section allows the reaction scheme to be simplified, thus avoiding the introduction of the stabilizer, and consequently reducing the costs.

Figure 9:
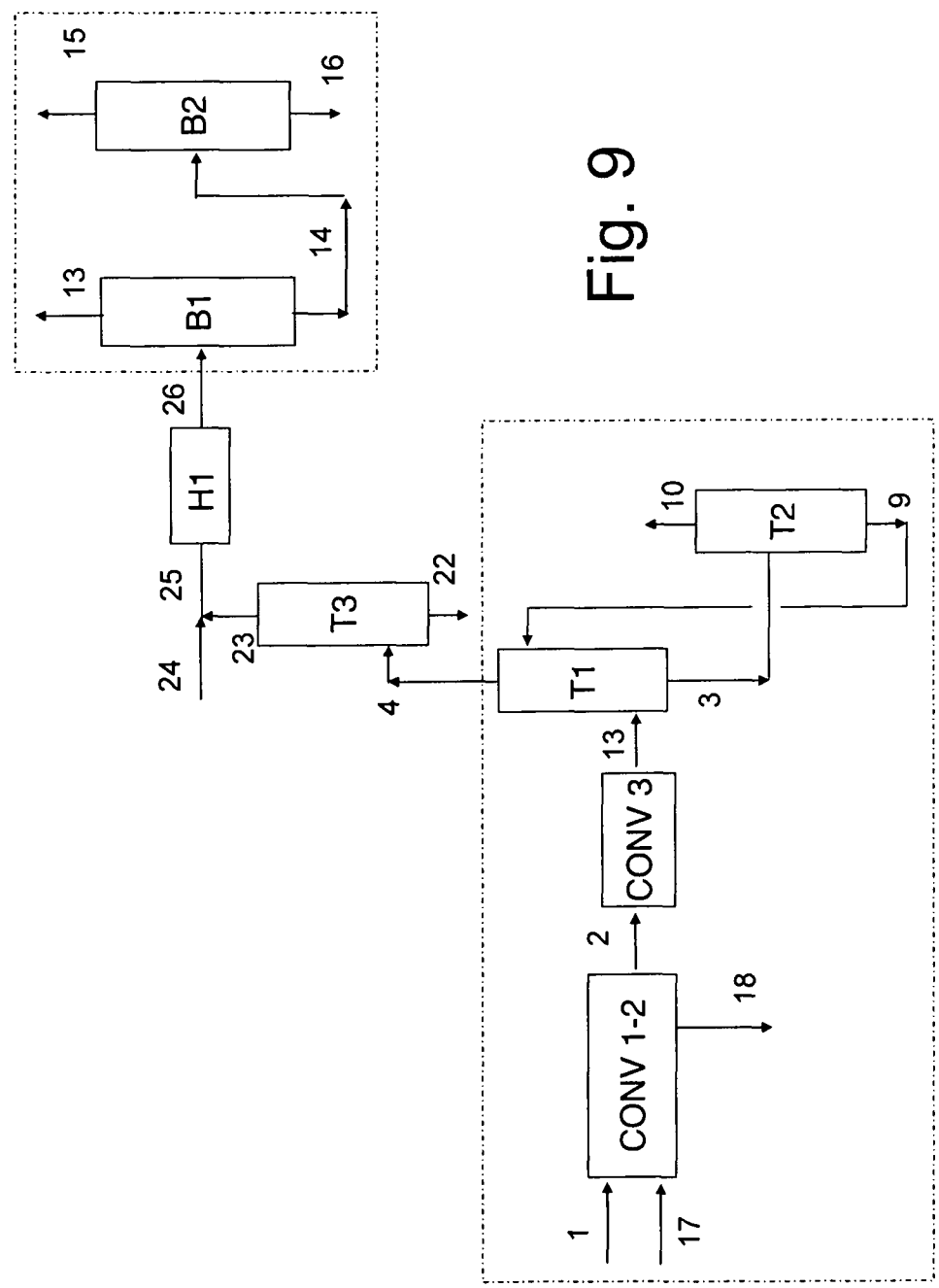

In this new configuration, in fact, as shown in FIG. 9, the C$_4$ hydrocarbons (23) leaving the column T3 for the removal of the oxygenated compounds, produced in CONV 3 and which could act as poisons for the hydrogenation catalyst, are sent (25) together with the hydrogen (24) to the hydrogenation section (H1). The effluent of this section (26) is then sent directly to the first separation column B1 which also acts as stabilizer as it allows not only the light compounds but also the excess hydrogen to be recovered in the distillate (13). The 1-butene, on the other hand, is recovered from the top (15) of the column B2.

Figure 10:
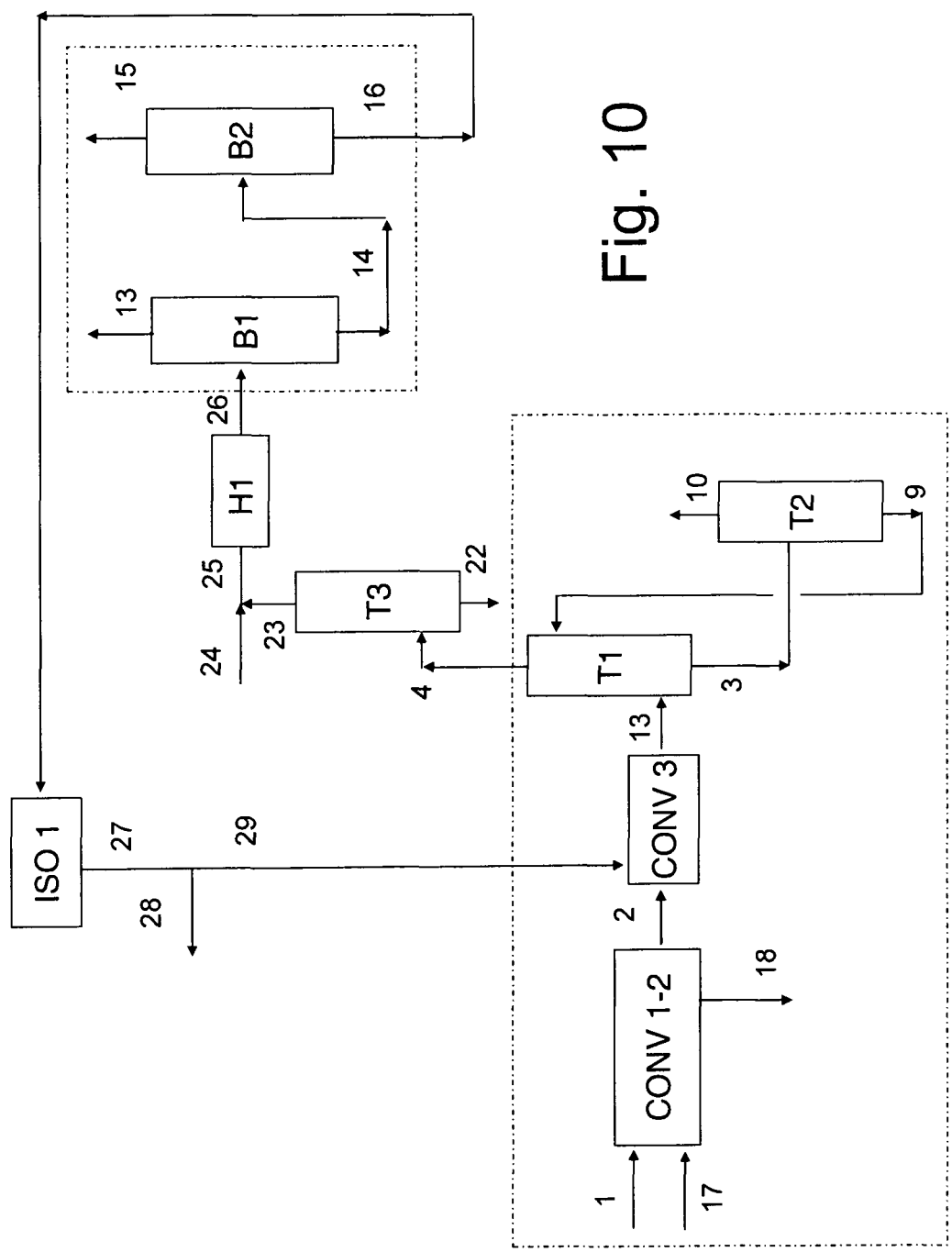

In the configuration illustrated in FIG. 10, the 1-butene is recovered as distillate (15) of the column B2 whose bottom product (16), mainly containing 2-butenes and n-butane, forms the feeding of the bond isomerization section ISO 1 where the 2-butenes are selectively converted to 1-butene (until thermodynamic equilibrium is reached) at temperatures ranging from 400 to 600° C.

The mixture leaving (27) this section is partially purged (28) to avoid the possible accumulation of saturated inert products, and is first sent (29) to the CONV 3 stage and is subsequently sent (23), after the complete removal of the oxygenated products in T1 and T3, to the hydrogenation stage in order to quantitatively remove first the isobutene and then the butadiene.

Figure 11:
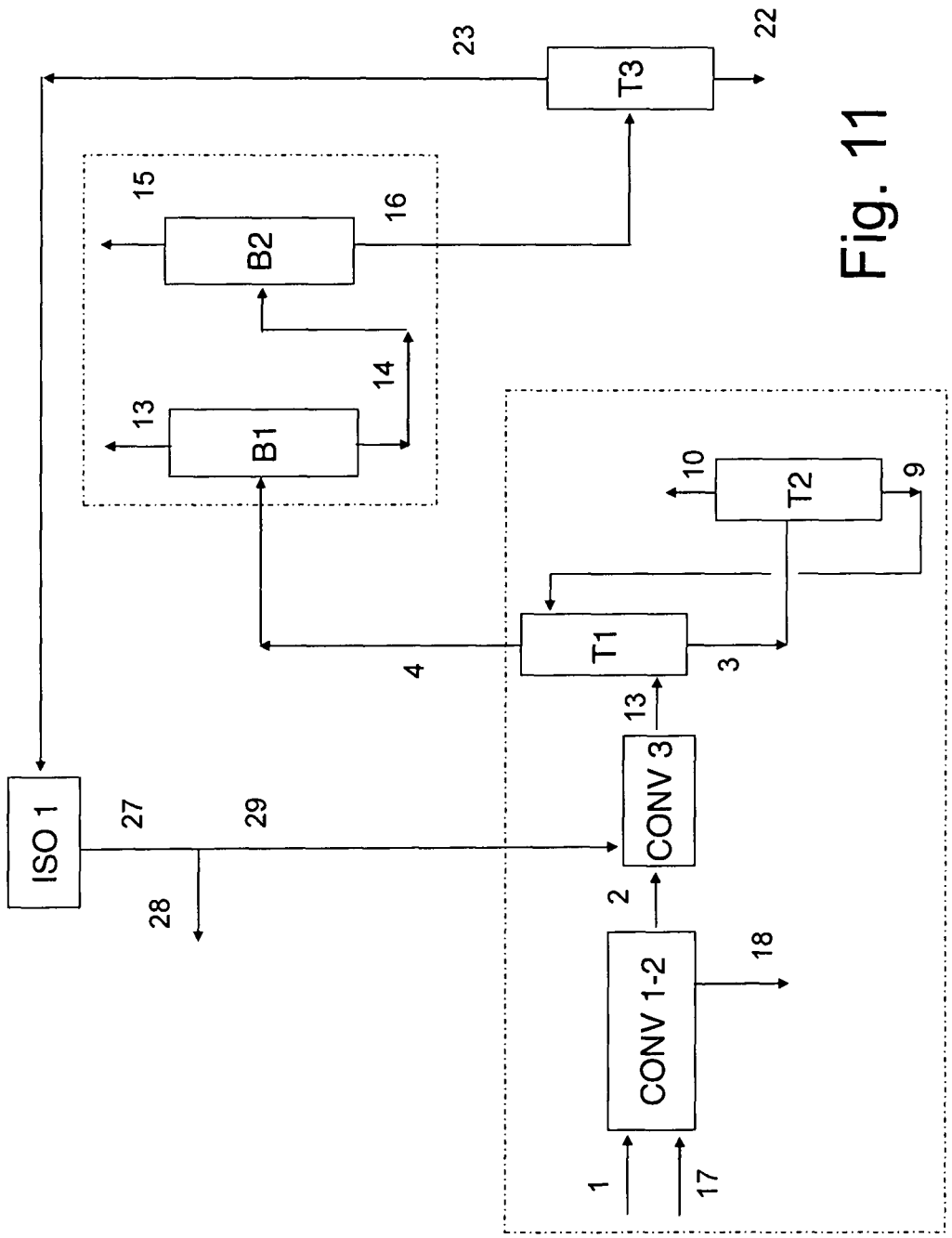
Figure 12:
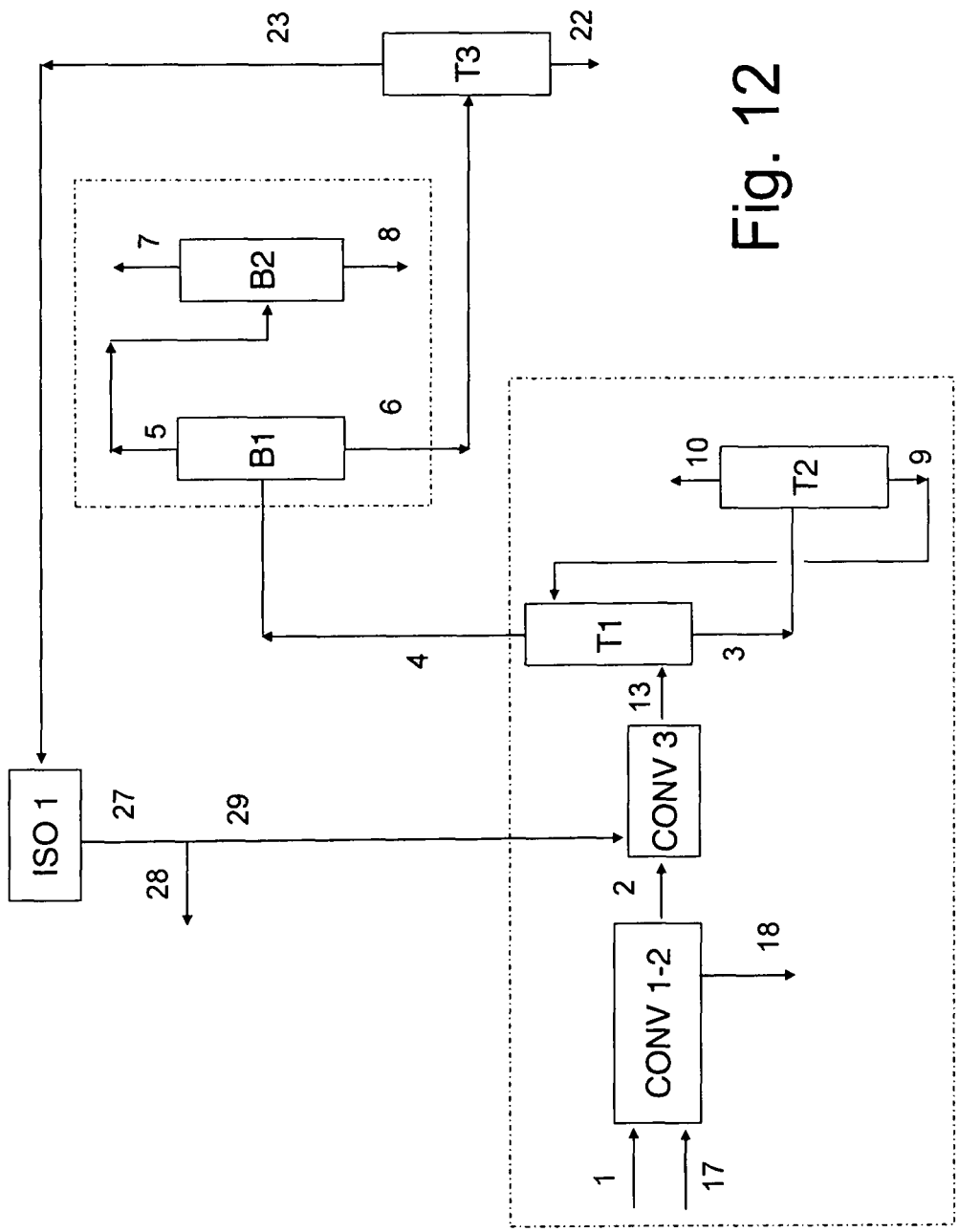

If an extremely selective catalyst is used in the isomerization section, which is capable of limiting the formation of butadiene, making the insertion of the hydrogenation section useless, the alternative configurations indicated in FIGS. 11 and 12 can be adopted, in which the column T3, for removing the oxygenated products formed in CONV 3, does not treat the whole C$_4$ charge but only the reduced stream (16) of FIG. 11 and (6) of FIG. 12, mainly containing 2-butenes and n-butane.

Figure 13:
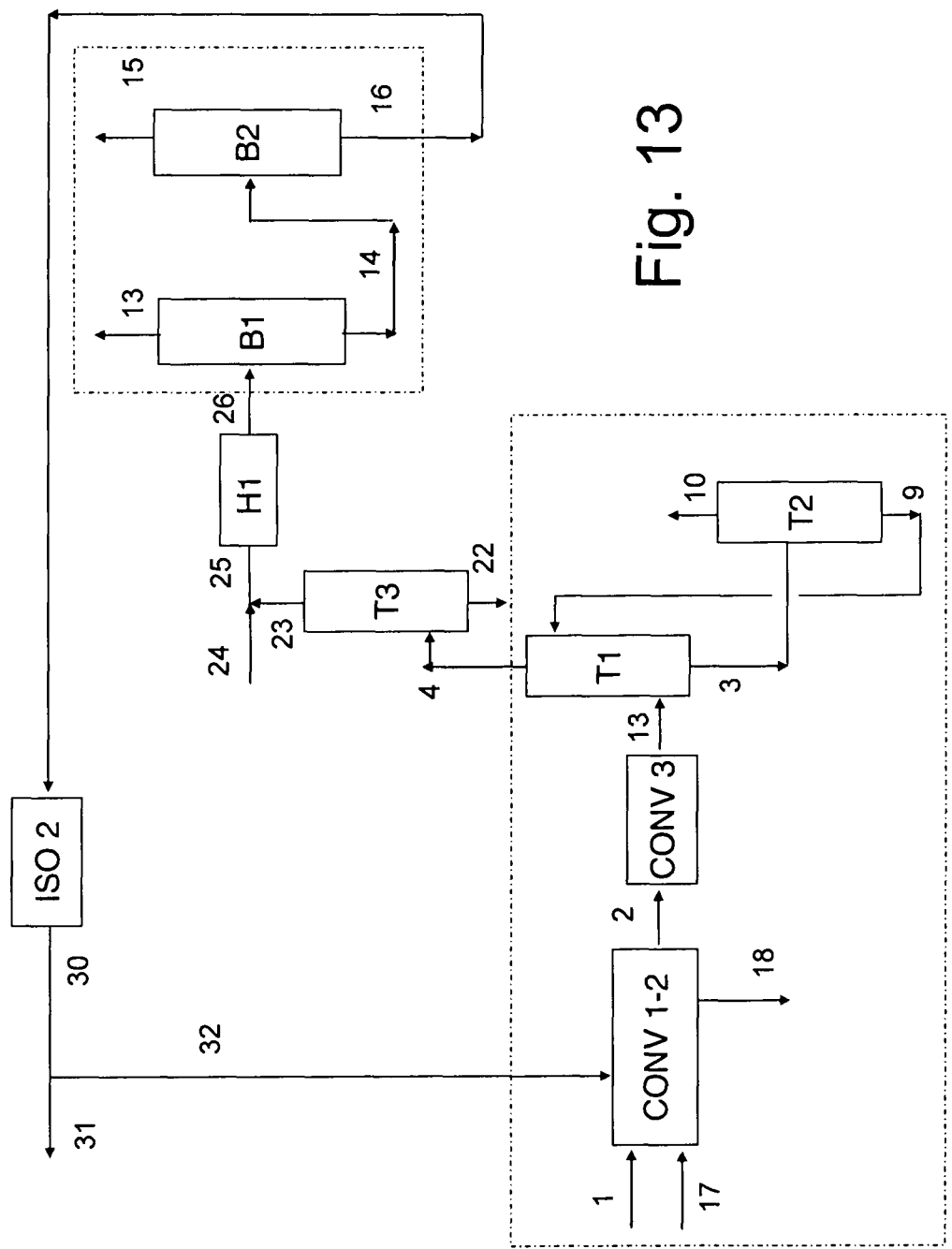

An even more complete plant scheme is that shown in FIG. 13 which envisages the introduction of a skeletal isomerization section ISO 2 of the 2-butenes in order to also increase the production of ETBE in addition to that of 1-butene.

In this case, therefore, the stream (16), mainly containing 2-butenes and n-butane, collected from the bottom of the column B2 for the recovery of the 1-butene (15), is sent to the skeletal isomerization section ISO-2; the isomerized product (30) (enriched in isobutene and 1-butene according to the thermodynamic equilibrium) is partially purged (stream 31), to avoid the accumulation of saturated inert products, and then sent (32) to the conversion section CONV 1-2 of the ETBE production plant. Also in this case, the contemporaneous presence of the two additional conversion sections CONV 3 and H1 allows a 1-butene to be obtained according to specification.

Figure 14:
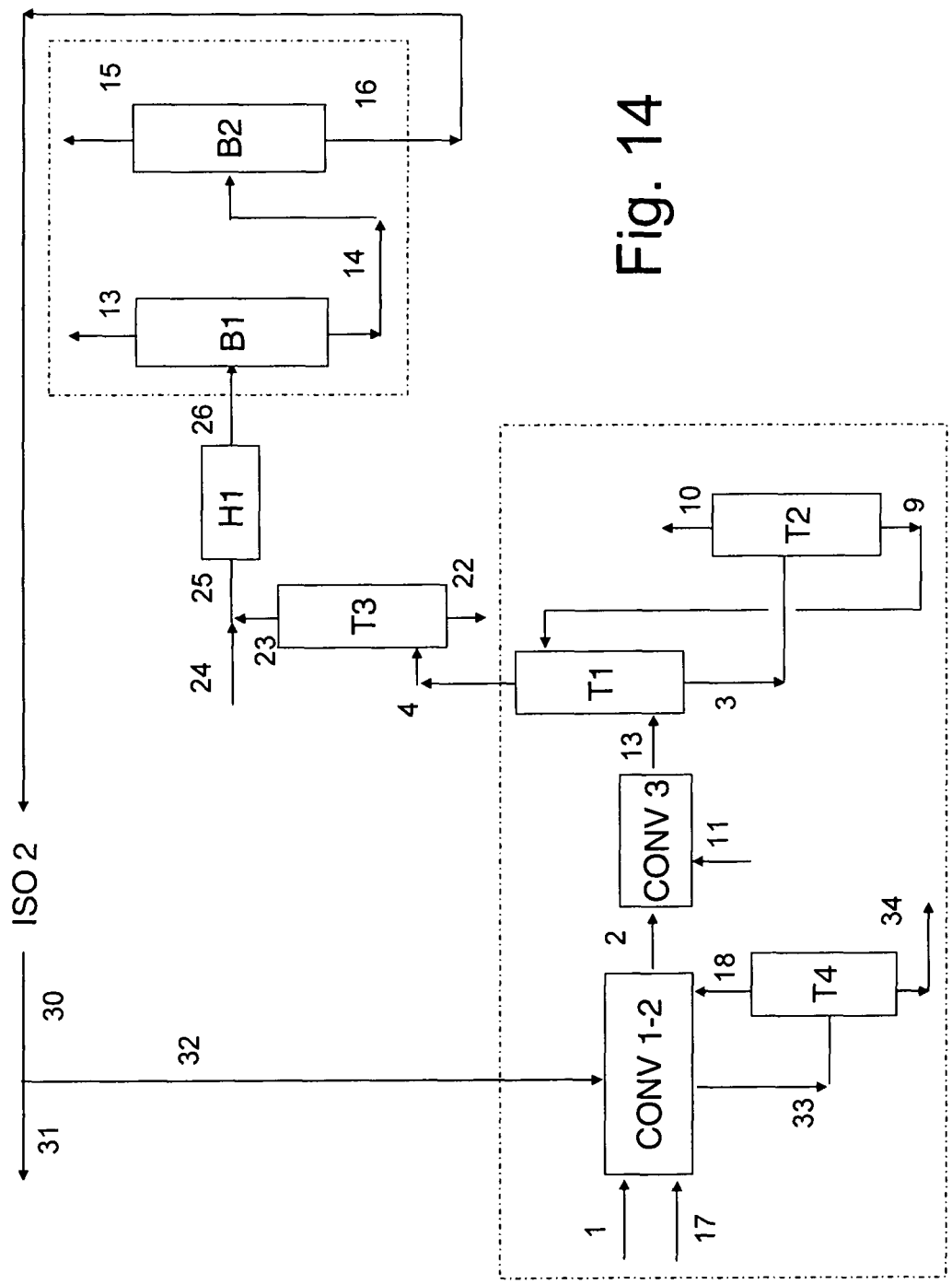

Finally, FIG. 14 shows a process scheme in which the skeletal isomerization is always present, but the isobutene conversion section CONV 1-2 consists of a selective dimerization carried out using oxygenated products as moderators of the acidity of the catalyst.

In the specific case of FIG. 14, using a mixture of alcohols (methanol) and ether (MTBE) as moderator, according to what is indicated in the patent GB 2325237, a new column T4 must also be introduced for the treatment of the stream (33) which, in the case of the dimerization reaction of isobutene, is a mixture of MTBE/dimerstrimers of isobutene. The distillate (18) of T4 containing MTBE is recycled to the section CONV 1-2 whereas the bottom product (34) containing dimers and trimers is the plant product.

In this particular scheme, in order to complete the conversion of isobutene, at the same time avoiding an excessive loss of 1-butene in the codimerization and isomerization reactions to 2-butenes, it is convenient to use the etherification reaction to MTBE (CONV 3), adding further methanol (ii) to the stream (2) of C$_4$ products leaving the section CONV 1-2, should its concentration not be sufficient.

The mixture leaving CONV 3 is then sent in the following order: to the washing column T1 (stream 13), to the removal column of the oxygenated products T3 (stream 4), to the hydrogenation H1 (stream 23) and finally to the fractionation section (stream 26). The 1-butene is recovered as distillate (15) from the column B2 whereas the bottom product (16) of this column forms the feed of the isomerization section ISO 2. The bottom product (22) of the column T3 containing MTBE produced in CONV 3, can be recycled to the section CONV 1-2, to compensate possible losses of ether in the plant, or used alternatively in other ways.

Optionally in the last reaction section CONV 3, in order to complete the conversion of isobutene, the water addition reaction can be used; in this way the isobutene is transformed into TBA, which, in the purification sections, has a behaviour analogous to the ether and is then recovered as bottom product of the column T3 in the previous schemes.

Some examples are now provided for a better illustration of the invention, it being understood, however, that the same invention is not limited thereby.

EXAMPLE 1

This example shows the limits of a 1-butene recovery plant, having a configuration similar to that shown in FIG. 1, if ethanol is used instead of methanol in the isobutene conversion section (etherification reaction).

Assuming that 100 Kg/hour of $C_4$ charge is fed (stream 1 of FIG. 1) having the following composition:

| | |
|---|---|
| Isobutene | 46% wt |
| 1-Butene | 30% wt |
| iso + n-Butane | 8% wt |
| 2-Butenes | 15% wt |
| $C_3$ and $C_5$ | 1% wt | and using a double-stage etherification plant configuration for the removal of isobutene, it is possible to obtain conversions of isobutene of 99.8% in the case of the production of MTBE but only 99% in the case of ETBE, as shown in Table 4.

TABLE 4

| | Case: Methanol | Case: Ethanol |
|---|---|---|
| MTBE, Kg/h | 72.1 | — |
| ETBE, Kg/h | — | 83.0 |
| Isobutene conversion, % | 99.8 | 99.0 |
| Isobutene in residual $C_4$, % | 0.17 | 0.83 |
| Isobutene in 1-Butene, % wt | 0.30 | 1.47 |

Upon passing therefore from methanol to ethanol, there is a clear increase in the overall production of ether, due to the effect of the higher molecular weight of the ethanol, but the total conversion of isobutene decreases with a consequent increase in the concentration of isobutene in the residual $C_4$ and production of a 1-butene outside specification.

EXAMPLE 2

This example, instead, shows how the use of the process of the present invention allows the conversion of isobutene to be kept constant in the passage from MTBE to ETBE, consequently continuing to produce a polymer grade 1-butene.

The use of an additional isobutene conversion section, in fact, according to what is shown in FIG. 3, allows, with respect to a traditional MTBE case, a slight increase in both the production of ether and the conversion of isobutene, consequently succeeding in obtaining a 1-butene with a higher degree of purity as shown in table 5.

TABLE 5

| | MTBE Synthesis FIG. 1 | Modified ETBE synthesis FIG. 3 |
|---|---|---|
| Isobutene conversion, % | 99.80 | 99.84 |
| Ether, Kg/h | 72.1 | 83.7 |
| Isobutene in residual $C_4$, % | 0.17 | 0.14 |
| Isobutene in 1-Butene, % wt | 0.30 | 0.25 |

EXAMPLE 3

This example shows the possible integration of a classical 1-butene recovery scheme (etherification+fractionation) with the additional conversion sections of isobutene and skeletal isomerization of the stream of $C_4$ heavy, mainly containing 2-butenes and n-butane.

A feeding of 100 Kg/hour of $C_4$ feedstock is still assumed having the following composition:

| | |
|---|---|
| Isobutene | 46.0% wt |
| 1-Butene | 30.0% wt |
| iso + n-Butane | 8.0% wt |
| 2-Butenes | 15.0% wt |
| 1,3-Butadiene | 0.1% wt |
| $C_3$ and $C_5$ | 1.0% wt | with a reaction scheme similar to that shown in FIG. 13 and a relatively high 1-butene recovery (90%), value close to the limit in industrial practice for this technology.

With this new scheme, it is therefore possible to be able to increase both the productions of ETBE and of 1-butene as shown in table 6, at the same time maintaining the products quality specifications unaltered; it is obviously necessary to draw a limited purge (30%) of the stream sent to the isomerization section to avoid the accumulation of saturated inert hydrocarbons.

TABLE 6

| | ETBE 3 stages FIG. 3 | ETBE 3 stages + Skeletal isom. FIG. 13 |
|---|---|---|
| Conv. Isobutene | 99.84 | 99.84 |
| ETBE, Kg/h | 83.7 | 92.2 |
| Isobutene in residual $C_4$, % | 0.14 | 0.09 |
| Isobutene in 1-Butene, % w | 0.25 | 0.22 |
| 1-Butene produced, Kg/h | 27.1 | 30.1 |

The presence of the selective hydrogenation unit ensures that the specification of 1-butene is respected also for the butadiene content, as shown in Table 7.

TABLE 7

| | |
|---|---|
| 1,3-Butadiene in stream 1, % wt | 0.100 |
| 1,3-Butadiene in stream 15, % wt | 0.120 |
| 1,3-Butadiene in stream 18, % wt | 0.001 |
| 1,3-Butadiene in 1-Butene, % wt | 0.002 |

The invention claimed is:

1. A process, comprising:
an initial conversion stage of converting isobutene from a FCC or stream cracking C4 hydrocarbon mixture comprising isobutene, n-butane, iso-butane, 1,3-butadiene, 1-butene, and a 2-butene by performing at least one of: etherifying the isobutene with an alcohol; dimerizing the isobutene in the presence of an alcohol; dimerizing the isobutene in the presence of water; and dimerizing the isobutene in the presence of an ether, wherein the initial conversion stage is conducted in two reaction steps, each reaction step occurring by (i) performing the converting in at least one reactor, optionally with intermediate cooling, and then immediately (ii) performing a single distillation in a distillation column that is separate from the at least one reactor and is suitable for recovery of an initial reaction product;

then, immediately following the initial conversion stage a further conversion stage of completely removing isobutene from the initial reaction product in a reactor or reactors in series, thereby producing a further reaction product comprising at least one oxygenated compound comprising dimethyl ether;

recovering excess alcohol if present in the initial reaction product or in the further reaction product;

removing the dimethyl ether and any other oxygenated compounds from the further reaction product produced in the further conversion stage, by distillation in a distillation column downstream therefrom; and an additional stage of selectively hydrogenating a diene from the further reaction product in at least one reactor situated immediately upstream of a recovery stage that is performed by recovering 1-butene with at least a first distillation column having an outflow that is an inflow to a second distillation column, thereby obtaining a high-purity 1-butene.

2. The process according to claim 1, wherein the initial conversion stage of converting isobutene comprises etherifying the isobutene with a linear alcohol.

3. The process according to claim 1, wherein the initial conversion stage of converting isobutene comprises selectively dimerizing the isobutene in the presence of a linear alcohol, a branched alcohol, an alkyl ether, or any combination thereof.

4. The process according to claim 3, wherein the isobutene is selectively dimerized in the presence of a branched alcohol having a number of carbon atoms of from 3 to 6.

5. The process according to claim 3, wherein the isobutene is selectively dimerized in the presence of an alkyl ether having a number of carbon atoms of from 5 to 10.

6. The process according to claim 1, wherein the further conversion stage comprises reacting the isobutene with a linear alcohol.

7. The process according to claim 2 or 6, wherein the linear alcohol has a number of carbon atoms of between 1 and 5.

8. The process according to claim 1, wherein the further conversion stage comprises reacting the isobutene with water.

9. The process according to claim 1, wherein the recovering of the excess alcohol comprises recovering the excess alcohol in two columns, of which a first column is a washing column with water.

10. The process according to claim 1, wherein the recovering of the excess alcohol comprises recovering the excess alcohol in an absorption system with molecular sieves.

11. The process according to claim 1, wherein the further conversion stage occurs before the recovery stage.

12. The process according to claim 1, wherein the further conversion stage occurs before the recovering of the excess alcohol.

13. The process according to claim 1, wherein the dimethyl ether and any other oxygenated compounds produced in the further conversion stage are removed with at least one distillation column situated downstream of the further conversion stage.

14. The process according to claim 1, wherein the removing of the dimethyl ether and any other oxygenated compounds produced in the further conversion stage comprises feeding the distillation column with a C4 hydrocarbon stream comprising 2-butene and n-butane.

15. The process according to claim 1, wherein the first distillation column of the recovery stage stabilizes the additional stage of selectively hydrogenating the diene.

16. The process according to claim 1, further comprising:
a bond isomerization stage of bond isomerizing a stream comprising 2-butenes and n-butane, following the recovery stage.

17. The process according to claim 1, further comprising:
a skeletal isomerization stage of skeletal isomerizing a stream comprising 2-butenes and n-butane, following the recovery stage.

18. The process according to claim 1, wherein the first and second distillation columns of the recovery stage are thermally integrated.

19. The process according to claim 1, further comprising:
providing a reboiler heat to one distillation column of the recovery stage from a total or partial condensation of a stream from the top of another distillation column of the recovery stage.

20. The process according to claim 1, further comprising:
providing a reboiler heat to one distillation column of the recovery stage and to a distillation column for removal of heavy products in the further conversion stage from a total or partial condensation of a stream from the top of another distillation column of the recovery stage.

21. The process according to claim 9 or 18, wherein the first and second distillation columns of the recovery stage are thermally integrated with an alcohol recovery column.

22. The process according to claim 21, further comprising:
providing a partial or total condensation of a vapor from a top of the alcohol recovery column as a reboiler to the first and second distillation columns of the recovery stage.

23. The process according to claim 22, further comprising:
providing a reboiler heat to the first and second distillation columns of the recovery stage by a total or partial condensation of the vapor from the top of the alcohol recovery column and from the first or the second distillation column of the recovery stage.

24. A process, comprising:
an initial conversion stage of converting isobutene from a FCC or stream cracking C4 hydrocarbon mixture comprising isobutene, n-butane, iso-butane, 1,3-butadiene, 1-butene, and a 2-butene by performing at least one of: etherifying the isobutene with an alcohol; dimerizing the isobutene in the presence of an alcohol; dimerizing the isobutene in the presence of water; and dimerizing the isobutene in the presence of an ether, wherein the initial conversion stage is conducted in two reaction steps, each reaction step occurring by (i) performing the converting in at least one reactor, optionally with intermediate cooling, and then immediately (ii) performing a single distillation in a distillation column that is separate from the at least one reactor and is suitable for recovery of an initial reaction product;

then, immediately following the initial conversion stage, a further conversion stage of completely removing isobutene from the initial reaction product in a reactor or reactors in series, thereby producing a further reaction product comprising at least one oxygenated compound comprising dimethyl ether;

recovering excess alcohol if present in the initial reaction product or in the further reaction product;

removing the dimethyl ether and any other oxygenated compounds from the further reaction product produced in the further conversion stage, by distillation in a distillation column downstream therefrom; and a recovery stage that is performed by recovering 1-butene with at least a first distillation column having an outflow that is an inflow to a second distillation column, thereby obtaining a high-purity 1-butene.

25. The process according to claim 1, wherein the recovery stage is performed such that the outflow of the first distillation column is a bottom product comprising the 1-butene and a mixture of heavy compounds, and the high-purity 1-butene is obtained as a distillate of the second distillation column.

26. The process according to claim 3, wherein the initial conversion stage comprises dimerizing the isobutene in the presence of a linear alcohol having a number of carbon atoms of between 1 and 5.

27. The process of claim 1, wherein each reaction step of the initial conversion stage occurs by (i) performing the converting in the at least one reactor, then immediately (ii) performing the intermediate cooling of reactor contents, and then immediately (iii) performing the single distillation of the reactor contents in the distillation column that is separate from the at least one reactor and is suitable for recovery of the initial reaction product.

28. The process of claim 24, wherein each reaction step of the initial conversion stage occurs by (i) performing the converting in the at least one reactor, then immediately (ii) performing the intermediate cooling of reactor contents, and then immediately (iii) performing the single distillation of the reactor contents in the distillation column that is separate from the at least one reactor and is suitable for recovery of the initial reaction product.

* * * * *

UNITED STATES PATENT AND TRADEMARK OFFICE
CERTIFICATE OF CORRECTION

PATENT NO. : 10,774,020 B2
APPLICATION NO. : 13/144101
DATED : September 15, 2020
INVENTOR(S) : Marco Di Girolamo et al.

Page 1 of 1

It is certified that error appears in the above-identified patent and that said Letters Patent is hereby corrected as shown below:

On the Title Page

Item (75) the 3rd Inventor's city is misspelled. Item (30), the Foreign Application Priority Data information is incorrect. Item (75) and Item (30) should read:

--(75) Inventors: Marco Di Girolamo, San Donato Milanese (IT)
　　　　　　　　Maura Brianti, Busto Arsizio (IT)
　　　　　　　　Massimo Conte, Peschiera Borromeo (IT)

(30)　　Foreign Application Priority Data
Jan. 13, 2009　(IT)..................... MI2009A000027--

Signed and Sealed this
Twenty-seventh Day of October, 2020

Andrei Iancu
*Director of the United States Patent and Trademark Office*